US009139864B2

(12) United States Patent
Krizman

(10) Patent No.: US 9,139,864 B2
(45) Date of Patent: Sep. 22, 2015

(54) C-SRC SELECTED REACTION MONITORING ASSAY

(71) Applicant: Expression Pathology, Inc., Rockville, MD (US)

(72) Inventor: David B. Krizman, Gaithersburg, MD (US)

(73) Assignee: EXPRESSION PATHOLOGY, INC., Rockville, MD (US)

( * ) Notice: Subject to any disclaimer, the term of this patent is extended or adjusted under 35 U.S.C. 154(b) by 0 days.

(21) Appl. No.: 13/754,146

(22) Filed: Jan. 30, 2013

(65) Prior Publication Data

US 2013/0131195 A1 May 23, 2013

Related U.S. Application Data

(63) Continuation of application No. PCT/US2011/045960, filed on Jul. 29, 2011.

(60) Provisional application No. 61/369,411, filed on Jul. 30, 2010.

(51) Int. Cl.
*G01N 24/00* (2006.01)
*C12Q 1/48* (2006.01)
*G01N 33/68* (2006.01)

(52) U.S. Cl.
CPC ............ *C12Q 1/485* (2013.01); *G01N 33/6848* (2013.01); *G01N 2333/91205* (2013.01)

(58) Field of Classification Search
None
See application file for complete search history.

(56) References Cited

U.S. PATENT DOCUMENTS

| 6,503,914 | B1 | 1/2003 | Benish et al. |
| 7,501,286 | B2 | 3/2009 | Gygi et al. |
| 2009/0136971 | A1 | 5/2009 | Krizman et al. |

FOREIGN PATENT DOCUMENTS

WO   WO-2004080579 A2   9/2004

OTHER PUBLICATIONS

Prieto et al., Liquid Tissue: proteomic profiling of formalin-fixed tissues, BioTechniques 38, Jun. 2005, pp. S32-S35.*
Mange et al., Liquid Chromatography—Tandem and MALDI Imaging Mass Spectrometry Analyses of RCL2/CS100-Fixed, Parafffin-Embedded Tissues: Proteomics Evaluatin of an Alternate Fixative for Biomarker Discovery, Journal of Proteome Research 2009, 8, pp. 5619-5628.*
Chen et al.: "Quantification of [beta]-Catenin Signaling; Components in Colon Cancer Cell Lines, Tissue Sections, and; Microdissected Tumor Cells using Reaction Monitoring Mass; Spectrometry", Journal of Proteome Research, vol. 9, No. 8, Jun. 30, 2010, pp. 4215-4227.
Hood B L et al.: "Proteomic analysis of formalin-fixed prostate cancer tissue", Molecular & Cellular Proteomics, American Society for Biochemistry and Molecular Biology, vol. 4, No. 11, Nov. 1, 2005, pp. 1741-1753.
Kirkpatrick D S et al: "The absolute quantification strategy: a general procedure for the quantification of proteins and post-translational modifications", Methods: A Companion to Methods in Eniymology, Academic Press Inc., New York, NY, US, vol. 35, No. 3, Mar. 1, 2005, pp. 265-273.
Krizman D et al.: "PP126 Quantitative protein analysis in FFPE tissue: Application to the tissue microenvironment", European Journal of Cancer. Supplement, Pergamon, Oxford, GB, vol. 7, No. 4, Oct. 1, 2009, pp. 21-22.
Taylor Petal.: "PP118 Detection and quantification of EGF receptor phosphorylation in formalin-fixed tumor sections by selected/multiple reaction monitoring mass spectrometry", European Journal of Cancer. Supplement, Pergamon, Oxford, GB, vol. 7, No. 4, Oct. 1, 2009, p. 31.
Ballif, et al.: "Quantitative phosphorylation profiling of the ERK/p90 ribosomal S6 kinase-signaling cassette and its targets, the tuberous sclerosis tumor suppressors," PNAS, vol. 102, No. 3, Jan. 18, 2005, pp. 667-672.
Extended European Search Report for Application EP11813272.9; Applicant Expression Pathology, Inc. Mail Date Feb. 7, 2014; 10 pages.
Gerber, et al.: Absolute quantification of proteins and phosphoproteins from cell lysates by tandem MS,: PNAS, vol. 100, No. 12, Jun. 10, 2003, pp. 6940-6945.
Guzel, et al.: "Multiple Reaction Monitoring Assay for Pre-eclampsia Related Calcyclin Peptides in Formalin Fixed Paraffin Embedded Placenta," Journal of Proteome Research, Oct. 26, 2010, pp. A-I.
Hawkridge, et al.: "Quantitative mass spectral evidence for the absence of circulating brain natriuretic peptide (BNP-32) in severe human heart failure," PNAS, vol. 102, No. 48, Nov. 29, 2005, pp. 17442-17447.
International Search Report for International Application PCT/US11/45960; Applicant Expression Pathology, Inc., Mail Date Jan. 5, 2012; pp. 5.

(Continued)

*Primary Examiner* — Gary W Counts
(74) *Attorney, Agent, or Firm* — Perkins Coie LLP

(57) ABSTRACT

Objective quantitation of the c-Src protein directly in cancer patient tissue can aid in determining the aggressiveness of an individual patient's tumor as well as help make more informed decisions about choice of therapy. However, the c-Src protein is currently analyzed directly in formalin fixed patient tissue only by immunohistochemistry methodology which is at best subjectively semi-quantitative. This invention describes an objective quantitative assay for the c-Src protein using mass spectrometry as the analytical methodology. Specific peptides, experimentally discovered characteristics about the peptides, and experimentally established assay conditions based on those peptide characteristics are provided for use in a mass spectrometry-based Selected Reaction Monitoring (SRM) assay in order to measure relative or absolute quantitative levels of c-Src directly in a protein preparation obtained from a formalin fixed cancer patient tissue sample.

16 Claims, No Drawings

(56) References Cited

OTHER PUBLICATIONS

Bagnato, et al.: "Proteomic Analysis of Human Coronary Atherosclerotic Plaque: A Feasibility Study of Direct Tissue Proteomics by Liquid-Chromatography and Tandem Mass Spectrometry," The American Society for Biochemistry and Molecular Biology Inc., Mar. 27, 2007.

Chen, et al.: "Supporting Information Chen et al. "Quantification of [beta]-Catenin Signaling Components in Colon Cancer Cell Lines, Tissue Sections, and Microdissected Tumor Cells using Reaction Monitoring Mass Spectrometry"", Journal of Proteome Research, Aug. 6, 2010, Retrieved from internet Jan. 28, 2014, http://pubs.acs.org/doi/suppl/10.1021/pr1005197/suppl_file/pr1005197_si_001.pdf.

Williamson, et al.: "Automated Identification and Quantification of Protein Phosphorylation Sites by LC/MS on a Hybrid Triple Quadrupole Linear Ion Trap Mass Spectrometer," The American Society for Biochemistry and Molecular Biology, Inc., Jun. 23, 2008, pp. 337-346.

* cited by examiner

SEQUENCE LISTING

<160> NUMBER OF SEQ ID NOS: 16

<210> SEQ ID NO 1
<211> LENGTH: 14
<212> TYPE: PRT
<213> ORGANISM: Homo sapiens

<400> SEQUENCE: 1

Gly Pro Ser Ala Ala Phe Ala Pro Ala Ala Ala Glu Pro Lys
1               5                   10

<210> SEQ ID NO 2
<211> LENGTH: 20
<212> TYPE: PRT
<213> ORGANISM: Homo sapiens

<400> SEQUENCE: 2

Ala Gly Pro Leu Ala Gly Gly Val Thr Thr Phe Val Ala Leu Tyr Asp
1               5                   10                  15

Tyr Glu Ser Arg
            20

<210> SEQ ID NO 3
<211> LENGTH: 8
<212> TYPE: PRT
<213> ORGANISM: Homo sapiens

<400> SEQUENCE: 3

Thr Glu Thr Asp Leu Ser Phe Lys
1               5

<210> SEQ ID NO 4
<211> LENGTH: 9
<212> TYPE: PRT
<213> ORGANISM: Homo sapiens

<400> SEQUENCE: 4

Leu Leu Leu Asn Ala Glu Asn Pro Arg
1               5

```
<210> SEQ ID NO 5
<211> LENGTH: 6
<212> TYPE: PRT
<213> ORGANISM: Homo sapiens

<400> SEQUENCE: 5

Gly Thr Phe Leu Val Arg
1               5

<210> SEQ ID NO 6
<211> LENGTH: 14
<212> TYPE: PRT
<213> ORGANISM: Homo sapiens

<400> SEQUENCE: 6

Gly Ala Tyr Cys Leu Ser Val Ser Asp Phe Asp Asn Ala Lys
1               5                   10

<210> SEQ ID NO 7
<211> LENGTH: 11
<212> TYPE: PRT
<213> ORGANISM: Homo sapiens

<400> SEQUENCE: 7

Leu Asp Ser Gly Gly Phe Tyr Ile Thr Ser Arg
1               5                   10

<210> SEQ ID NO 8
<211> LENGTH: 15
<212> TYPE: PRT
<213> ORGANISM: Homo sapiens

<400> SEQUENCE: 8

Thr Gln Phe Asn Ser Leu Gln Gln Leu Val Ala Tyr Tyr Ser Lys
1               5                   10                  15

<210> SEQ ID NO 9
<211> LENGTH: 8
<212> TYPE: PRT
<213> ORGANISM: Homo sapiens

<400> SEQUENCE: 9

His Ala Asp Gly Leu Cys His Arg
1               5

<210> SEQ ID NO 10
<211> LENGTH: 8
<212> TYPE: PRT
<213> ORGANISM: Homo sapiens

<400> SEQUENCE: 10

Gly Ser Leu Leu Asp Phe Leu Lys
1               5

<210> SEQ ID NO 11
<211> LENGTH: 13
<212> TYPE: PRT
<213> ORGANISM: Homo sapiens

<400> SEQUENCE: 11

Ala Ala Asn Ile Leu Val Gly Glu Asn Leu Val Cys Lys
1               5                   10
```

```
<210> SEQ ID NO 12
<211> LENGTH: 8
<212> TYPE: PRT
<213> ORGANISM: Homo sapiens

<400> SEQUENCE: 12

Val Ala Asp Phe Gly Leu Ala Arg
1               5

<210> SEQ ID NO 13
<211> LENGTH: 10
<212> TYPE: PRT
<213> ORGANISM: Homo sapiens

<400> SEQUENCE: 13

Leu Ile Glu Asp Asn Glu Tyr Thr Ala Arg
1               5                   10

<210> SEQ ID NO 14
<211> LENGTH: 10
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 14

Leu Ile Glu Asp Asn Glu Tyr Thr Ala Arg
1               5                   10

<210> SEQ ID NO 15
<211> LENGTH: 11
<212> TYPE: PRT
<213> ORGANISM: Homo sapiens

<400> SEQUENCE: 15

Trp Thr Ala Pro Glu Ala Ala Leu Tyr Gly Arg
1               5                   10

<210> SEQ ID NO 16
<211> LENGTH: 16
<212> TYPE: PRT
<213> ORGANISM: Homo sapiens

<400> SEQUENCE: 16

Ser Asp Val Trp Ser Phe Gly Ile Leu Leu Thr Glu Leu Thr Thr Lys
1               5                   10                  15
```

C-SRC SELECTED REACTION MONITORING ASSAY

This application is a continuation of International Application No. PCT/US2011/045960, filed Jul. 29, 2011, which claims the benefit of U.S. Provisional Application No. 61/369,411, filed Jul. 30, 2010, both of which are entitled "c-Src Selected Reaction Monitoring Assay" and name as an inventor David B. Krizman, each of which applications is herein incorporated by reference in its entirety. This application also contains a sequence listing submitted electronically via EFS-web, which serves as both the paper copy and the computer readable form (CRF) and consists of a file entitled "01152 8017US01 Seq Listing", which was created on Jan. 29, 2013, which is 3,072 bytes in size, and which is also incorporated by reference in its entirety.

INTRODUCTION

Specific peptides are provided that are derived from subsequences of the c-Src protein, also known as CSK and which will be referred to as Src. Specific characteristics about each peptide are provided, which includes the peptide sequence and fragmentation/transition ions for reliable, accurate and consistent analysis in mass spectrometric analysis. Also described is the use of those peptides in a mass spectrometry-based Selected Reaction Monitoring (SRM), which can also be referred to as a Multiple Reaction Monitoring (MRM) assay. This SRM assay can be used to measure relative or absolute quantitative levels of one or more of the specific peptides from the Src protein and therefore provide a means of measuring the amount of the Src protein by mass spectrometry in a given protein preparation obtained from a biological sample.

More specifically, the SRM assay can measure these peptides directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by references in their entirety. The methods described in U.S. Pat. No. 7,473,532 may conveniently be carried out using Liquid Tissue® reagents available from Expression Pathology, Inc. (Rockville, Md.).

Results from the SRM assay can be used to correlate accurate and precise quantitative levels of the Src protein with the specific cancer of the patient from whom the tissue was collected. This not only provides diagnostic information about the cancer, but also permits a physician or other medical professional to determine appropriate therapy for the patient. Such an assay that provides diagnostically important information about levels of protein expression in a diseased tissue or other patient sample is termed a companion diagnostic assay. For example, such an assay can be designed to diagnose the stage or degree of a cancer and determine which therapeutic agent, or course of therapy, to which a patient is most likely to respond with a positive outcome.

The assays described herein measure relative or absolute levels of specific unmodified peptides from the Src protein and also can measure absolute or relative levels of specific modified peptides from the Src protein. Examples of modifications include phosphorylated amino acid residues and glycosylated amino acid residues that are present on the peptides.

Relative quantitative levels of the Src protein are determined by the SRM methodology whereby the chromatographic peak area (or the peak height if the peaks are sufficiently resolved) of an individual peptide, or multiple peptides, from the Src protein in one biological sample is compared to the chromatographic peak area determined for the same identical Src peptide, or peptides, using the same methodology in one or more additional and different biological samples. In this way, the amount of a particular peptide, or peptides, from the Src protein, and therefore the amount of the Src protein, is determined relative to the same Src peptide, or peptides, across 2 or more biological samples under the same experimental conditions. In addition, relative quantitation can be determined for a given peptide, or peptides, from the Src protein within a single sample by comparing the chromatographic peak area for that peptide by SRM methodology to the chromatographic peak area for another and different peptide, or peptides, from a different protein, or proteins, within the same protein preparation from the biological sample. In this way, the amount of a particular peptide from the Src protein, and therefore the amount of the Src protein, is determined relative one to another within the same sample. These approaches generate quantitation of an individual peptide, or peptides, from the Src protein to the amount of another peptide, or peptides, between samples and within samples wherein the amounts as determined by chromatographic peak area are relative one to another, regardless of the absolute weight to volume or weight to weight amounts of the Src peptides in the protein preparation from the biological sample. Relative quantitative data about individual chromatographic peak areas between different samples are normalized to the amount of protein analyzed per sample. Relative quantitation can be performed across many peptides simultaneously in a single sample and/or across many samples to gain insight into relative protein amounts, one peptide/protein with respect to other peptides/proteins.

Absolute quantitative levels of the Src protein are determined by the SRM methodology whereby the chromatographic peak area of an individual peptide from the Src protein in one biological sample is compared to the chromatographic peak area of a spiked internal standard, where the internal standard is a synthetic version of the same exact Src peptides that contains one or more amino acid residues labeled with one or more heavy isotopes. The internal standard is synthesized so that when analyzed by mass spectrometry it generates a predictable and consistent signature chromatographic peak that is different and distinct from the native Src peptide chromatographic signature peak. Thus when the internal standard is spiked into a protein preparation from a biological sample in known amounts and analyzed by mass spectrometry, the signature chromatographic peak area of the native peptide is compared to the signature chromatographic peak area of the internal standard peptide, and this numerical comparison indicates either the absolute molarity or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in cohorts of individual samples.

The assay methods can be used to aid diagnosis of the stage of cancer, for example, directly in patient-derived tissue, such as formalin fixed tissue, and to aid in determining which therapeutic agent, and which therapeutic strategy, would be most advantageous for use in treating that patient. Cancer tissue that is removed from a patient either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient tissue. Moreover, the expression level of the protein(s) can be determined and compared to a "normal" or reference level found in healthy tissue or tissue that shows a different stage/grade of cancer. This information can then be used to assign a stage or grade to a specific cancer and can be matched to a strategy for treating the patient based on the determined levels of specific proteins. Matching specific information about levels of the Src protein, as determined by an SRM assay, to a treatment strategy that is based on levels of these proteins in cancer cells derived from the patient defines what has been termed a personalized medicine approach to treating disease. The assay methods described herein form the foundation of a personalized medicine approach by using analysis of proteins from the patient's own tissue as a source for diagnostic and treatment decisions.

DETAILED DESCRIPTION

In principle, any predicted peptide derived from the Src protein, for example by digesting with a protease of known specificity (e.g. trypsin), can be used as a surrogate reporter to determine the abundance of the Src protein in a sample using a mass spectrometry-based SRM assay. Similarly, any predicted peptide sequence containing an amino acid residue at a site that is known to be potentially modified in the Src protein also might potentially be used to assay the extent of modification of the Src protein in a sample. Surprisingly, however, the present inventors have found that many potential peptide sequences are unsuitable or ineffective for use in mass spectrometry-based SRM assays. The peptides might, for example, be difficult to detect by mass spectrometry, or may be unstable to the conditions used to obtain the peptides from the parent protein. This is especially found to be the case when interrogating protein lysates prepared from formalin fixed tissue using the Liquid Tissue® protocol provided in U.S. Pat. 7,473,532. Unexpectedly it was found to be advantageous to experimentally identify preferred modified and unmodified peptides in actual Liquid Tissue® lysates in order to develop a reliable and accurate SRM assay for the Src protein. Preferred modified and unmodified peptides for use in the mass spectrometric methods described herein (e.g., SRM), including identifying presence (or absence) and/or amount of proteins in formalin fixed tissues, are hereinafter known as optimized peptides.

In general, peptides were derived from the Src protein in the course of the protease digestion of the proteins within a complex Liquid Tissue® lysate prepared from cells procured from formalin fixed patient tissue. The Liquid Tissue® lysates were then analyzed by mass spectrometry to determine those peptides derived from the Src protein that are preferably detected and analyzed by mass spectrometry (i.e., optimized preferred modified and unmodified peptides). The results are employed to identify a specific subset of preferred peptides selected for their suitability in mass spectrometric analysis. The procedure employed permits experimental determination of peptides or peptides fragments that ionize most effectively, and which provide suitable data for resulting peptide transition fragment ions that can be identified and quantitated in a Liquid Tissue® preparation from formalin fixed patient tissue. These results can then be compared to results obtained by mass spectrometry analysis of the recombinant protein that has been digested with the same protease, or proteases, in order to confirm the existence of preferred or optimized peptides and their resulting transition fragments.

In addition to their suitability in mass spectrometric analysis, the ability of labeled versions of preferred (or more specifically optimized) peptides to withstand the conditions used in Liquid Tissue® preparation protocols is an important determinant as to which peptides are preferred (or optimized where formalin fixed tissue is used) for qualitative or quantitative analyzing of tissues by mass spectrometry (e.g., SRM). This latter property depends not only on the amino acid sequence of the peptide but also to the ability of a modified residue within a peptide to survive in modified form during the sample preparation. The assay method described below can be used to identify the peptides from the Src protein that are preferred or optimized for identifying and quantitating protein expression or modification in patient samples, and more specifically patient samples derived from formalin fixed tissue, by mass spectrometry-based SRM assay.

Assay Method for the Identification of Peptides from the Src protein

1. Identification of a preferred (or optimized) fragment peptide, or preferred (or optimized) fragment peptides, for the Src protein
   a. Treat purified Src protein with the Liquid Tissue® reagents and protocol using a protease or proteases, (that may or may not include trypsin), to digest the Src protein. Analyze some (e.g., 10, 20, 30 or 40%), most (e.g., more than 50, 60, 70, 80, 90, 95, 98 or 99%), or all resulting protein fragments by tandem mass spectrometry and identify all fragment peptides from the Src protein, where individual fragment peptides do not contain any peptide modifications such as phosphorylations or glycosylations.
   b. Prepare a Liquid Tissue® protein lysate from a formalin fixed biological sample using the same protease or proteases as utilized when preparing the purified Src protein (that may or may not include trypsin), to digest most, or all proteins. Analyze some, most, or all resulting protein fragments from some, most, or all proteins in the mixture by tandem mass spectrometry and identify some, most, or all fragment peptides specifically from the Src protein, where individual fragment peptides do not contain any peptide modifications such as phosphorylations or glycosylations. Analyze some, most, or all resulting protein fragments from some, most, or all the proteins by tandem mass spectrometry and identify some, most, or all fragment peptides from the Src protein that carry peptide modifications such as for example phosphorylated or glycosylated residues.
   c. Some, most or all peptides generated by a specific digestion method from the entire, full length Src protein potentially can be measured, but preferred peptides are those that are identified by mass spectrometry from analysis of the purified proteins and that also are identified directly in a complex Liquid Tissue® protein lysate prepared from a histopathologically fixed biological sample (e.g., optimized peptides can be measured where the tissue is formalin fixed).
   Peptides that are post-translationally modified, and their specific fragment characteristics, can be considered preferred or optimized peptides and assayed where the relative levels of the modified peptides are determined in the same manner as determining relative amounts of unmodified peptides for the Src protein.
2. Mass Spectrometry Assay for Fragment Peptides from the Src protein
   a. A Selected Reaction Monitoring (SRM), or also known as a Multiple Reaction Monitoring (MRM), assay is conducted on a triple quadrupole mass spectrometer for each individual preferred or optimized fragment peptides identified in a Liquid Tissue® lysate from the Src protein may be developed as follows:
  i. Determine retention time for each fragment peptide of Src for at least one suitable fractioning method including but not limited to gel electrophoresis, liquid chromatography, capillary electrophoresis, isoelectric separation chromatography, nano-reversed phase liquid chromatography, high performance liquid chromatography, or reverse phase high performance liquid chromatography.
  ii. Identify suitable fragment transition ions to monitor for one or more fragment peptides based on the highest signal to noise ratio and/or the lowest standard deviation between replicate analyses for use in Liquid Tissue® samples prepared from histopathologically fixed tissue (e.g., formalin fixed tissues).
 b. Perform SRM/MRM analysis so that the amount of the fragment peptide, or peptides, of the Src protein that is detected, as a function of specific peak area (or height where suitable) from an SRM/MRM mass spectrometry analysis, reflects both the relative and absolute amount of the protein in a particular Liquid Tissue® lysate.
  i. Relative quantitation is achieved by: comparing the (e.g., electrophoretic chromatographic, etc.) peak area for a fragment peptide to the peak area of the same fragment peptide, or other fragment peptides from other proteins, in other samples derived from different and separate biological sources, where the chromatographic peak area comparison between the samples for a peptide fragment are normalized to amount of protein analyzed in each sample. Comparison of the separation peak area for a given fragment peptide to the separation peak areas from other fragment peptides derived from different proteins within the same sample can be performed to normalize changing levels of one protein to levels of other proteins that do not change their levels of expression under various conditions (e.g., cellular conditions). Relative quantitation can be applied to unmodified fragment peptides and modified fragment peptides, where the modifications include but are not limited to phosphorylation and/or glycosylation, and where the relative levels of modified peptides are determined in the same manner as determining relative amounts of unmodified peptides.
  ii. Absolute quantitation of a given peptide is achieved by comparing the peak area for a given fragment peptide in an individual biological sample to the peak area of an internal fragment peptide standard spiked into the protein lysate from the biological sample. The analysis of the given peptide and the standard spiked into the sample can be conducted simultaneously. The internal standard can be a labeled version (e.g., a labeled synthetic version) consisting of the exact amino acid sequence of the fragment peptide that is being interrogated. The labeled standard is spiked into a sample in known amounts, and the chromatographic peak area can be determined for both the internal fragment peptide standard and the native fragment peptide in the biological sample separately, followed by comparison of both peak areas and deriving the absolute amount of the native peptide as compared to the absolute amount of the spiked peptide standard. Absolute quantitation can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
3. Associate Fragment Peptide Quantitation to Cancer Diagnosis and/or Treatment
 a. Perform relative and/or absolute quantitation of fragment peptide levels of the Src protein and associate results with the stage/grade/status of cancer in patient tumor tissue; and/or
 b. Perform relative and/or absolute quantitation of fragment peptide levels of the Src protein and correlate with specific and different treatment strategies, wherein this correlation has been, or can be demonstrated in the future, to correlate with outcome to various treatment strategies through correlation studies across cohorts of patients and tissue from those patients. Once either previously established correlations are confirmed by this assay, or new correlations established, the assay method can be used to associate quantitative results for the Src protein in patient tissue to more effective patient treatment strategy.

TABLE 1 c-Src Peptide Sequences and Specific Characteristics

| SEQ ID | Peptide sequence | Monoisotopic Mass | Precursor charge state | Precursor m/z | Product Transition m/z | Ion Type |
|---|---|---|---|---|---|---|
| SEQ ID NO: 1 | GPSAAFAPAAAEPK | 1284.65828 | 2 | 642.83 | 1043.55 | y11 |
|  |  |  | 2 | 642.83 | 972.51 | y10 |
|  |  |  | 2 | 642.83 | 901.48 | y9 |
|  |  |  | 2 | 642.83 | 754.41 | y8 |
|  |  |  | 2 | 642.83 | 683.37 | y7 |
| SEQ ID NO: 2 | AGPLAGGVTTFVALYDYESR | 2087.0444 | 3 | 696.35 | 832.35 | y6 |
|  |  |  | 3 | 696.35 | 669.28 | y5 |
|  |  |  | 3 | 696.35 | 554.26 | y4 |
|  |  |  | 3 | 696.35 | 391.19 | y3 |
|  |  |  | 3 | 696.35 | 262.15 | y2 |
|  |  |  | 2 | 1044.03 | 1115.54 | y9 |
|  |  |  | 2 | 1044.03 | 1016.47 | y8 |
|  |  |  | 2 | 1044.03 | 945.43 | y7 |
|  |  |  | 2 | 1044.03 | 832.35 | y6 |
|  |  |  | 2 | 1044.03 | 669.28 | y5 |

TABLE 1-continued c-Src Peptide Sequences and Specific Characteristics

| SEQ ID | Peptide sequence | Monoisotopic Mass | Precursor charge state | Precursor m/z | Product Transition m/z | Ion Type |
|---|---|---|---|---|---|---|
| SEQ ID NO: 3 | TETDLSFK | 940.4622 | 2 | 470.73 | 839.41 | y7 |
| | | | 2 | 470.73 | 710.37 | y6 |
| | | | 2 | 470.73 | 609.32 | y5 |
| | | | 2 | 470.73 | 494.30 | y4 |
| | | | 2 | 470.73 | 381.21 | y3 |
| SEQ ID NO: 4 | LLLNAENPR | 1039.58947 | 2 | 520.30 | 813.42 | y7 |
| | | | 2 | 520.30 | 700.34 | y6 |
| | | | 2 | 520.30 | 586.29 | y5 |
| | | | 2 | 520.30 | 386.21 | y3 |
| | | | 2 | 520.30 | 272.17 | y2 |
| SEQ ID NO: 5 | GTFLVR | 692.40899 | 2 | 346.71 | 534.34 | y4 |
| | | | 2 | 346.71 | 387.27 | y3 |
| | | | 2 | 346.71 | 274.19 | y2 |
| | | | 2 | 346.71 | 175.12 | y1 |
| SEQ ID NO: 6 | GAYCLSVSDFDNAK | 1489.66277 | 2 | 773.85 | 1095.53 | y10 |
| | | | 2 | 773.85 | 982.45 | y9 |
| | | | 2 | 773.85 | 895.42 | y8 |
| | | | 2 | 773.85 | 796.35 | y7 |
| | | | 2 | 773.85 | 709.32 | y6 |
| SEQ ID NO: 7 | LDSGGFYITSR | 1215.60043 | 2 | 608.30 | 987.49 | y9 |
| | | | 2 | 608.30 | 786.41 | y6 |
| | | | 2 | 608.30 | 639.35 | y5 |
| | | | 2 | 608.30 | 476.28 | y4 |
| | | | 2 | 608.30 | 363.20 | y3 |
| SEQ ID NO: 8 | TQFNSLQQLVAYYSK | 1789.91193 | 3 | 597.31 | 843.46 | y7 |
| | | | 3 | 597.31 | 730.38 | y6 |
| | | | 3 | 597.31 | 631.31 | y5 |
| | | | 3 | 597.31 | 560.27 | y4 |
| | | | 3 | 597.31 | 397.21 | y3 |
| | | | 2 | 895.46 | 1099.58 | y9 |
| | | | 2 | 895.46 | 730.38 | y6 |
| | | | 2 | 895.46 | 631.31 | y5 |
| | | | 2 | 895.46 | 560.27 | y4 |
| | | | 2 | 895.46 | 397.21 | y3 |
| SEQ ID NO: 9 | HADGLCHR | 908.41554 | 2 | 483.22 | 828.38 | y7 |
| | | | 2 | 483.22 | 757.34 | y6 |
| | | | 2 | 483.22 | 642.31 | y5 |
| | | | 2 | 483.22 | 472.21 | y3 |
| | | | 2 | 483.22 | 175.12 | y1 |
| SEQ ID NO: 10 | GSLLDFLK | 892.51385 | 2 | 446.76 | 748.46 | y6 |
| | | | 2 | 446.76 | 635.38 | y5 |
| | | | 2 | 446.76 | 522.29 | y4 |
| | | | 2 | 446.76 | 407.27 | y3 |
| | | | 2 | 446.76 | 147.11 | y1 |
| SEQ ID NO: 11 | AANILVGENLVCK | 1343.73515 | 2 | 700.88 | 1031.56 | y9 |
| | | | 2 | 700.88 | 918.47 | y8 |
| | | | 2 | 700.88 | 819.40 | y7 |
| | | | 2 | 700.88 | 406.21 | y3 |
| | | | 2 | 700.88 | 307.14 | y2 |
| SEQ ID NO: 12 | VADFGLAR | 848.46248 | 2 | 424.73 | 749.39 | y7 |
| | | | 2 | 424.73 | 678.36 | y6 |
| | | | 2 | 424.73 | 563.33 | y5 |
| | | | 2 | 424.73 | 416.26 | y4 |
| | | | 2 | 424.73 | 246.16 | y2 |
| SEQ ID NO: 13 | LIEDNEYTAR | 1223.59026 | 2 | 612.30 | 997.42 | y8 |
| | | | 2 | 612.30 | 868.38 | y7 |
| | | | 2 | 612.30 | 753.35 | y6 |
| | | | 2 | 612.30 | 510.27 | y4 |
| | | | 2 | 612.30 | 347.20 | y3 |

TABLE 1-continued c-Src Peptide Sequences and Specific Characteristics

| SEQ ID | Peptide sequence | Monoisotopic Mass | Precursor charge state | Precursor m/z | Product Transition m/z | Ion Type |
|---|---|---|---|---|---|---|
| SEQ ID NO: 14 | LIEDNE(pY)TAR | 1303.55659 | 2 | 652.28 | 1077.39 | y8 |
| | | | 2 | 652.28 | 948.35 | y7 |
| | | | 2 | 652.28 | 833.32 | y6 |
| | | | 2 | 652.28 | 590.23 | y4 |
| | | | 2 | 652.28 | 347.20 | y3 |
| SEQ ID NO: 15 | WTAPEAALYGR | 1234.6215 | 2 | 617.81 | 947.49 | y9 |
| | | | 2 | 617.81 | 876.46 | y8 |
| | | | 2 | 617.81 | 579.32 | y5 |
| | | | 2 | 617.81 | 508.29 | y4 |
| | | | 2 | 617.81 | 395.20 | y3 |
| SEQ ID NO: 16 | SDVWSFGILLTELTTK | 1809.96329 | 2 | 905.49 | 1088.66 | y10 |
| | | | 2 | 905.49 | 918.55 | y8 |
| | | | 2 | 905.49 | 805.47 | y7 |
| | | | 2 | 905.49 | 692.38 | y6 |
| | | | 2 | 905.49 | 591.33 | y5 |

The invention claimed is:

1. A method for measuring the level of Src protein in a human biological sample of formalin-fixed tissue, comprising detecting at least one fragment peptide from Src in a protein digest prepared from said biological sample using mass spectrometry; and calculating the levels of the Src protein in said sample, wherein said at least one fragment peptide is selected from the group consisting of SEQ ID NO:3, SEQ ID NO:4, and SEQ ID NO:7, and wherein said measured level of the Src protein is independently selected from a relative level or an absolute quantitative level.

2. The method of claim 1, further comprising the step of fractionating said protein digest prior to detecting said at least one fragment peptide.

3. The method of claim 1, wherein said protein digest comprises a protease digest.

4. The method of claim 3, wherein said protein digest comprises a trypsin digest.

5. The method of claim 1, wherein the tissue is obtained from a tumor.

6. The method of claim 1, further comprising quantifying the Src fragment peptide, or peptides.

7. The method of claim 6, wherein quantifying the Src fragment peptide comprises comparing an amount of a Src fragment peptide selected from the group consisting of SEQ ID NO:3, SEQ ID NO:4, and SEQ ID NO:7, in said sample to the amount of the same Src fragment peptide in a different and separate biological sample from a different and separate primary and/or secondary tumor or tumors.

8. The method of claim 6, wherein quantifying the Src fragment peptide comprises comparing an amount of the Src fragment peptide to an internal standard peptide of known amount, wherein both the peptide in the biological sample and the internal standard peptide are selected from the group consisting of SEQ ID NO:3, SEQ ID NO:4, and SEQ ID NO:7.

9. The method of any of claim 8, wherein the internal standard peptide is an isotopically labeled peptide.

10. The method of claim 1, further comprising obtaining the biological sample from a subject, wherein detecting the Src fragment peptides in the protein digest indicates the presence of the Src protein and an association with cancer in the subject.

11. The method of claim 1, further comprising administering a therapeutically effective amount of a therapeutic agent targeted specifically to the Src protein or the level of Src protein, wherein selection of the therapeutic agent, or the amount of said agent used for treatment is based upon the level of the one or more of said Src fragment peptides in the biological sample.

12. The method of claim 11, wherein therapeutic agents include those that specifically bind to the Src protein and inhibit the biological activity of Src.

13. The method of claim 12, wherein detecting and quantitating the Src fragment peptides is combined with detecting and quantitating other peptides from other proteins so that the treatment decision about which agent or agents and/or the amount of said agent or agents used for treatment is based upon specific levels of the Src fragment peptides in combination with other peptides/proteins in the biological sample.

14. The method of claim 1 wherein said fragment peptide is SEQ ID NO:3.

15. The method of claim 1 wherein said fragment peptide is SEQ ID NO:4.

16. The method of claim 1 wherein said fragment peptide is SEQ ID NO:7.

* * * * *